(12) United States Patent
Gordon et al.

(10) Patent No.: US 8,240,260 B2
(45) Date of Patent: *Aug. 14, 2012

(54) APPARATUS FOR DELIVERING BENEFICIAL LIQUIDS AT STEADY RATE

(75) Inventors: John Howard Gordon, Salt Lake City, UT (US); Ashok V. Joshi, Salt Lake City, UT (US); Truman Wold, Paauilo, HI (US); Sai Bhavaraju, West Jordan, UT (US)

(73) Assignee: Microlin, LLC., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/281,282

(22) Filed: Oct. 25, 2011

(65) Prior Publication Data

US 2012/0037242 A1    Feb. 16, 2012

Related U.S. Application Data

(60) Division of application No. 12/550,050, filed on Aug. 28, 2009, now Pat. No. 8,061,280, which is a continuation-in-part of application No. 12/100,982, filed on Apr. 10, 2008, now Pat. No. 7,658,156.

(60) Provisional application No. 61/092,538, filed on Aug. 28, 2008.

(51) Int. Cl.
*A01C 23/02* (2006.01)
(52) U.S. Cl. ........................................ 111/7.3
(58) Field of Classification Search .................. 210/640, 210/641, 650, 652, 321.74, 321.83, 493.4, 210/494.1, 195.2, 257.2, 416.1, 417; 203/99, 203/91; 111/118, 200, 900, 7.1–7.4, 127
See application file for complete search history.

(56) References Cited

U.S. PATENT DOCUMENTS

| | | | |
|---|---|---|---|
| 4,838,862 A | 6/1989 | Baker et al. | |
| 4,874,388 A | 10/1989 | Wong et al. | |
| 4,898,582 A | 2/1990 | Faste | |
| 5,672,167 A | 9/1997 | Athayde et al. | |
| 5,798,119 A | 8/1998 | Herbig et al. | |
| 5,954,268 A | 9/1999 | Joshi et al. | |
| 6,139,750 A * | 10/2000 | Graham | 210/652 |

(Continued)

OTHER PUBLICATIONS

Choi, Byung Chul "International Search Report", International App. No. PCT/US2009/055432, (Apr. 19, 2010),1-5.

(Continued)

*Primary Examiner* — Christopher J. Novosad
(74) *Attorney, Agent, or Firm* — David Fonda

(57) ABSTRACT

An apparatus for delivering a beneficial agent is disclosed in one embodiment of the invention as including a water collection chamber. A water-transporting membrane is provided to communicate with the water collection chamber. An extraction chamber receives water through the water-transporting membrane, expanding the extraction chamber. A dispensing chamber, containing a beneficial agent, is configured to contract upon expanding the extraction chamber. This causes the dispensing chamber to expel the beneficial agent through a subterranean delivery channel, such as a rigid hollow spike. In certain embodiments, a rate adjustment mechanism may control the rate that water is received through the water-transporting membrane, thereby controlling the rate the beneficial agent is expelled. The water-transporting membrane has features that repel osmagent from passing through to the water collection chamber. The apparatus features steady rate performance without refreshing the water chamber and low temperature sensitivity.

12 Claims, 5 Drawing Sheets

U.S. PATENT DOCUMENTS

| | | | |
|---|---|---|---|
| 6,217,773 | B1 | 4/2001 | Graham |
| 6,923,800 | B2 | 8/2005 | Chen et al. |
| 7,658,156 | B2 * | 2/2010 | Wold et al. ............... 111/7.3 |
| 8,061,280 | B2 * | 11/2011 | Gordon et al. ............ 111/7.3 |
| 2002/0158156 | A1 | 10/2002 | Joshi et al. |
| 2005/0269266 | A1 | 12/2005 | Twardowski et al. |

OTHER PUBLICATIONS

Choi, Byung Chul "Written Opinion of the International Searching Authority", International App. No. PCT/US2009/055432, (Apr. 19, 2010),1-4.

* cited by examiner

APPARATUS FOR DELIVERING BENEFICIAL LIQUIDS AT STEADY RATE

CROSS-REFERENCE TO RELATED APPLICATION

The present application is a divisional application of, and claims priority to, U.S. patent application Ser. No. 12/550,050, filed Aug. 28, 2009 now U.S. Pat. No. 8,061,280, which was a continuation-in-part of U.S. patent application Ser. No. 12/100,982 filed Apr. 10, 2008 now U.S. Pat. No. 7,658,156 entitled "Apparatus and Method For Delivery Beneficial Agents to Subterranean Locations," which is hereby incorporated by reference. This application also claims priority to U.S. Provisional Patent No. 61/092,538 filed on Aug. 28, 2008 and entitled "Apparatus and Methods For Delivering Beneficial Liquids at Steady Rate," and which is also hereby incorporated by reference.

BACKGROUND

This invention relates to an apparatus for delivering beneficial liquids such as fragrances, deodorizers, sanitizers, pesticides and pest repellants at a steady rate for extended time periods using an osmotic pump and where the source of water for the osmosis typically is not continuously refreshed.

What is needed is an apparatus for delivering liquid beneficial agents, such as fragrances, de-odorizers, sanitizers, pesticides and pest repellants in a controlled, predictable manner. Ideally, such an apparatus would be suitable to disperse a wide variety of different beneficial liquids products which may be solutions, suspensions, or mixtures. Further needed is an apparatus for easily controlling the rate at which the beneficial agents are released.

Many have investigated delivering liquids using osmotic engines. In general, an osmagent is contained in a variable volume container that in part includes a semipermeable membrane and also communicates with a container containing a beneficial agent through a flexible diaphragm, piston or such. Upon activation, the semipermeable membrane is exposed to a source of water. Water flows through the semipermeable membrane into the osmagent container, expanding the volume, which in turn forces the beneficial agent to be expelled. In some cases the devices are implanted into the body of an animal or human where the body is the source of water. In other cases, the water is supplied from a reservoir contained in the device.

Herbig et al. in U.S. Pat. No. 5,798,119 disclosed a device used for delivering fluids such as fragrances and insecticides. They used a hydrophobic microporous separator to separate an osmagent from liquid water. Water vapor passes through the hydrophobic membrane from the liquid water to the osmagent, increasing the volume where the osmagent is located. The volume increase drives the delivery of the beneficial agent. A disadvantage of this approach is that water vapor pressure is very temperature dependant. For example, water vapor pressure is 20× higher at 50 C compared to 0 C. Looking at a narrower temperature range. The vapor pressure at 10 C is 56% lower than at 23 C and at 44 C the vapor pressure is 326% that of 23 C. Thus temperature variations will have a very large impact on the dispense rate with this type of system which is very undesirable in most cases.

Faste in U.S. Pat. No. 4,898,582 and Atahyde et al. in U.S. Pat. No. 5,672,167 disclosed drug infusion devices using osmosis where the water was contained within the device. These inventors disclosed systems utilizing cellulose ester or cellulose ether membranes such as cellulose acetate as the semipermeable membrane between the osmagent and the water source. An advantage of these membranes over the hydrophobic membranes disclosed by Herbig et al. is the fact that liquid water diffuses through the semipermeable membranes rather than water vapor. This significantly reduces the temperature sensitivity of the osmosis since the concentration of water is substantially unchanged over a temperature range as opposed to widely varying water vapor pressure. A disadvantage of these membranes is that while they are substantially semipermeable, they still have permeability to many potential osmagents. As a result, the osmagent can permeate into the water container as well as water diffusing into the osmagent container. While the diffusion of osmagent is small, the effect over time can be very large when the volume of water contained is near the same amount of liquid to be dispensed and especially if the time scale of delivery is long. As osmagent diffuses into the water container, the driving force for diffusion of water across the semipermeable membrane is reduced and the delivery rate declines over time.

Several inventors such as Wong et al. in U.S. Pat. No. 4,874,388 and Chen et al. in U.S. Pat. No. 6,923,800 disclose osmotically driven devices where the devices are implanted into the body of animal or man where the water is supplied by the body and where the concentration of the water near the semipermeable membrane remains nearly the same over time due to the active nature of the body. Wong et al. describe the use of "cellulosic polymers such as cellulose acetate, ethyl cellulose, methylcellulose, cellulose acetate butyrate, cellulose acetate propionate, blends of impermeable material and hydrophilic polymer or a molecular weight water soluble enhancer to render the material semipermeable". Chen et al. on the other hand disclosed using polyurethane materials which are somewhat permeable to water for low rate devices.

The prior art does not teach how to obtain steady fluxes of water through a semipermeable membrane where osmagent is on one side and a non continuously refreshed water source is opposite and where variation in rate due to changes in temperature are minimal.

SUMMARY OF THE INVENTION

Consistent with the foregoing, an apparatus for delivering a beneficial agent is disclosed in one embodiment of the invention as including a water chamber. A water-transporting membrane is provided to communicate with the water chamber. An extraction chamber receives water through the water-transporting membrane, expanding the extraction chamber. A dispensing chamber, containing a beneficial agent, is configured to contract upon expanding the extraction chamber. This causes the dispensing chamber to expel the beneficial agent in some cases to a disseminating feature which may be related to evaporating the liquid through a wicking emanator. In certain embodiments, a rate adjustment mechanism may control the rate that water is received through the water-transporting membrane, thereby controlling the rate the beneficial agent is expelled. The water chamber may be designed in an open fashion where the user can fill by pouring water into it, or the chamber may be enclosed to prevent water from spilling. If the water chamber is enclosed, the volume preferably is either variable through a flexible member or it may be variable by having a piston member. Alternatively the water chamber may be vented to prevent a partial vacuum from forming in the water chamber during discharge. The vent may have a hydrophobic microporous plug or membrane to prevent spillage.

The water transporting membrane in this invention is different from the prior art. A membrane feature desired is a structure that repels osmagent constituents but is also water permeable. An example of a membrane that has such a structure is an ion exchange membrane. The ion exchange membrane may have varying backbone structure and varying functional groups of a particular polarity. For example, the backbone structure may be fluoropolymer based or styrene divinyl benzene based. The membranes may also have a backing material made from a material such as poly vinyl chloride to increase burst strength. The functional groups may be positively charged like a quaternary ammonia group or negatively charged like a sulfonate group. If the functional group is positively charged, then the membrane is classified as an anionic exchange membrane and conversely if the functional group is negatively charged then the membrane is considered a cation exchange membrane. One advantage of using such membranes is that they are water permeable but have a structure that slows down diffusion of salts or polar molecules. Reducing the diffusion of the osmagent is advantageous where the water in the water chamber is not continuously refreshed because the driving force for osmosis is reduced when osmagent diffuses into the water chamber and rate decreases. Examples of ion exchange membranes are Nafion by Dupont, and several membranes by ASTOM Corporation such as Neosepta CMX, AMX, CIMS, CMB, AHA, ACM, ACS, AFN and AFX. Other ion exchange membrane manufacturers and brands include Selemion by Asahi Glass. In particular, Neosepta CMB has been found to work very well, allowing good water flux but very little salt diffusion. Using this particular membrane, with ammonium phosphate dibasic as osmagent, steady delivery rates were obtained with a non-refreshed water compartment.

Another example of membrane feature that repels osmagent constituents but is also water permeable are membranes that have a functional groups attached to the surface such as sulfonate group or quaternary ammonium groups with a charge that will reject a similarly charged anion or cation. Here conventional cellulosic type membranes could be modified by adding functional groups to the surface.

An activation feature may be included in the design to prevent exposure of water to the membrane until time of use. The activation may be the joining of the water chamber to the device. Activation features are discussed in U.S. Pat. Nos. 4,838,862 and 4,898,582, both of which are incorporated herein by reference, and could be used in this device.

The delivery rate of the device may be adjusted by including a feature which masks part of the membrane and can be adjusted by increasing or decreasing the exposure of the membrane to the water.

The water chamber may be filled with water or may be filled with a solution containing one or more constituents such as a salt that may prevent the solution from freezing during storage or operation.

In selected embodiments, the extraction chamber and the dispensing chamber are separated by a piston. In other embodiments, the extraction chamber and the dispensing chamber are separated by a flexible diaphragm. Where a flexible diaphragm is used, in selected embodiments, the flexible diaphragm may include several layers to prevent or reduce the diffusion of water through the diaphragm. In certain embodiments, a separator material, such as air or another gas or mixture of gases may be introduced between the layers to further prevent the water diffusion. In other embodiments, the flexible diaphragm may be coated with a water-impermeable material, such as metal, to prevent or reduce diffusion.

In other embodiments, the extraction chamber, the dispensing chamber, or both may be contained at least partially within a pouch. In certain embodiments, the pouch may be coated with a water-impermeable material, such as metal, to prevent water from diffusing there through.

In certain embodiments, the extraction chamber contains an osmotic medium, such as a salt or a saline solution, to draw water through the water-transporting membrane and into the extraction chamber through osmosis. In other embodiments, the apparatus may include a circuit to allow electrical current to flow through the water-transporting membrane, thereby allowing water to travel through the water-transporting membrane into the extraction chamber through electro-osmosis.

In another embodiment in accordance with the invention, a method for delivering a beneficial may include collecting water with a substantially open end of a water collection chamber. This water may be transported through a water-transporting membrane into an extraction chamber, thereby expanding the extraction chamber. This may cause a beneficial agent to be expelled from a dispensing chamber for delivery to a subterranean location.

In certain embodiments in accordance with the invention, multiple semipermeable membranes may be utilized between the water chamber and the extraction chamber to further reduce the diffusion of osmagent into the water chamber. Some of these membranes may be spatially separated from one another with liquid between. A combination of membranes that may be particularly useful for prevention of migration of osmagent is where at least one membrane has functional group with a polarity different than at least one other membrane, for example and anion exchange membrane can be used in combination with a cation exchange membrane.

The present invention provides improved apparatus and methods for delivering beneficial agents. The features and advantages of the present invention will become more fully apparent from the following description and appended claims, or may be learned by practice of the invention as set forth hereinafter.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings in which.

DETAILED DESCRIPTION OF THE INVENTION

The invention has been developed in response to the present state of the art and, in particular, in response to the problems and needs in the art that have not yet been fully solved by currently available devices for delivering liquid beneficial agents such as fragrances, de-odorizers, sanitizers, pesticides and pest repellants. Such devices either suffer from a decline in delivery performance over time to the point that the benefits are no longer rendered or when the devices are active and have acceptable performance, the devices are complex in nature which results in high cost. Accordingly, the invention has been developed to provide novel apparatus and methods for delivering liquid beneficial agents to target areas in a controlled and predictable manner and where impact of temperature variation is minimal. The features and advantages of the invention will become more fully apparent from the following description and appended claims and their equivalents, and also any subsequent claims or amendments presented, or may be learned by practice of the invention as set forth hereinafter. The devices can stand alone and do not require power or external connections.

Figures 1, 1A, 1B:
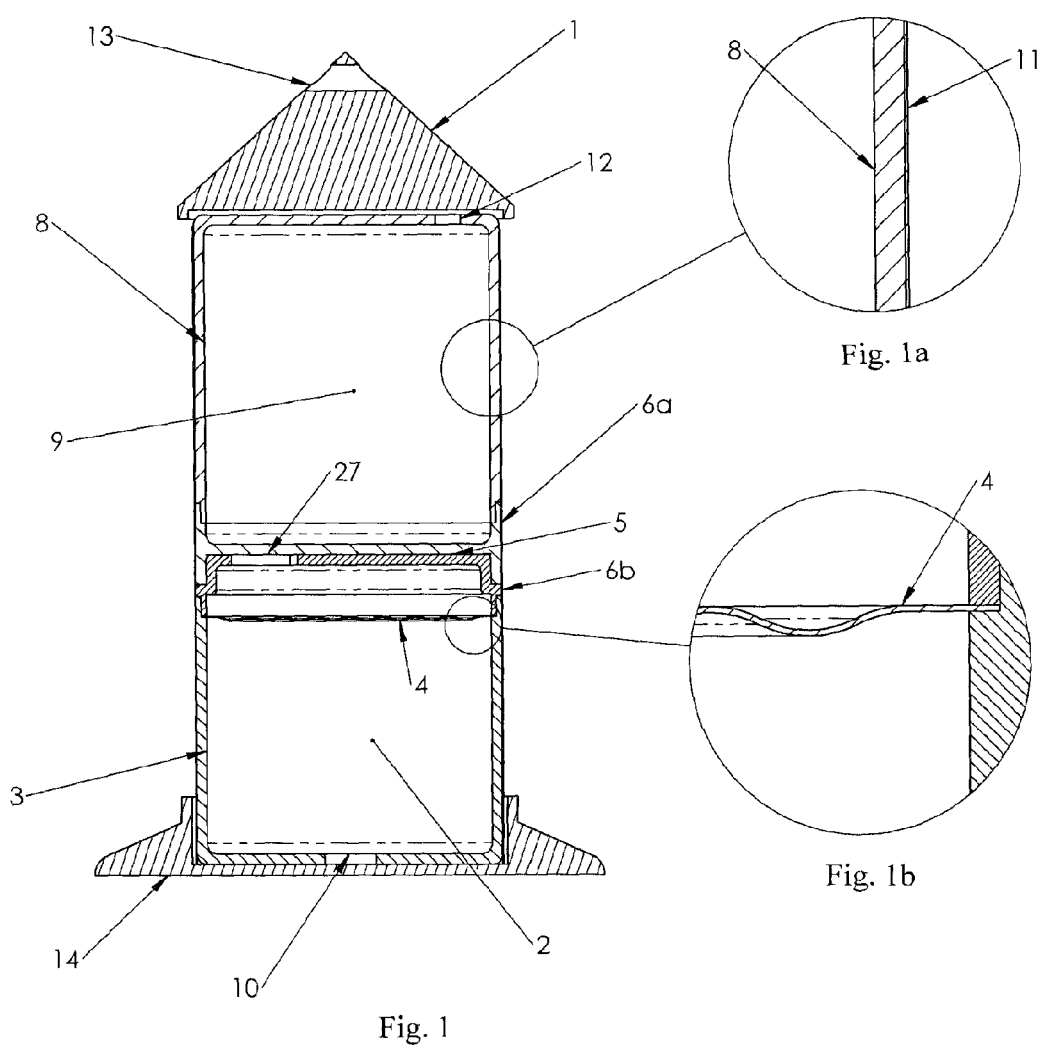
FIG. 1 is a schematic cutaway drawing of an embodiment of the invention.
FIG. 1a is a schematic cutaway drawing of a portion of the housing of FIG. 1.
FIG. 1b is a schematic cutaway drawing of a diaphragm of FIG. 1.

FIG. 1 schematically shows one embodiment of a device for delivering a beneficial agent 2. The beneficial agent 2 is in container 3 of substantially rigid walls with the exception of a flexible bellows 4 or diaphragm 4 that enables the volume of the container 3 to reduce. An ion exchange membrane 5 separates the flexible bellows 4 from the water 9 containing chamber 8. A first adjustment member 6a has openings 7 (not shown). Depending on the position of the adjustment member 6a relative to a second adjustment member 6b, the membrane 5 may be obscured or an increasingly greater area of the membrane 5 may be exposed to the water 9 upon activation. A mass of osmagent (not shown), is located between the flexible bellows 4 and the membrane 5. The bellows 4 preferably comprises or is coated by materials of low water permeability such as metal or barrier polymer such as metalized PET (polyethylene terephthalate), Halar, PCTFE (polychlorotrifluoroethylene). Other polymers with relatively low water permeability that may be used include HDPE (high density polyethylene), PP (polypropylene), PEEK (polyetheretherketone), PET and FEP (fluorinated ethylene propylene). Upon activation water 9 flows through the membrane 5 and increases the volume between the membrane 5 and the bellows 4. As this occurs, beneficial agent 2 is expelled through port 10. In this case a wick may transport the beneficial agent 2 away from the port 10 and up the side walls of the device 1 so the beneficial agent 2 may more readily evaporate. The device is housed in a structure with a base 14 and a hanger 13 to provide multiple sites where the device can be located in a space such as a room. The water container 8 has a vent 12 with a hydrophobic microporous film that allows air to enter the water container 8 as water 9 transports across the membrane. Alternatively the water container 8 could have a flexible wall or a piston such that the volume diminishes as the water 9 transports out of the container 8.

It is understood that the figure shows just one embodiment of the invention. The apparatus could also be constructed where the beneficial agent 2 is contained within a pouch or flexible bag that becomes compressed as the water 9 transports into the zone between the membrane 5 and the flexible bellows 4. Also, the bellows 4 could be replaced with a flexible diaphragm or piston such that an expansion zone containing the osmagent exists to receive the water 9 transporting across the membrane 5 and mechanically forces the beneficial agent 2 to be expelled from the apparatus 1.

In one embodiment, an apparatus to provide controlled delivery of a beneficial agent includes a water chamber, a water-transporting membrane in communication with the water collection chamber, an extraction chamber to receive water through the water-transporting membrane and into the extraction chamber, thereby expanding the extraction chamber, an osmagent in the extraction chamber, a dispensing chamber containing a beneficial agent and contracting in response to expanding the extraction chamber, and a port in communication with the dispensing chamber to deliver the beneficial agent.

In another embodiment, an apparatus to provide controlled delivery of a beneficial agent includes a water chamber, a water-transporting membrane in communication with the water collection chamber where the membrane has a membrane feature that repels one or more osmagent constituents, an extraction chamber to receive water through the water-transporting membrane and into the extraction chamber, thereby expanding the extraction chamber, an osmagent in the extraction chamber, a dispensing chamber containing a beneficial agent and contracting in response to expanding the extraction chamber, and a port in communication with the dispensing chamber to deliver the beneficial agent.

The osmagent repelling feature or structure of the membrane may be a functional group on the surface of the membrane, and may be of the class including a quaternary ammonium group or a sulfonate group, or combinations thereof. The osmagent repelling feature or structure of the membrane in one embodiment is a charged functional group within the membrane. The charged functional group within the membrane may be of the class including a sulfonate or a quaternary ammonium, or combinations thereof.

The membrane of the apparatus may be an ion exchange membrane. The ion exchange membrane in one embodiment may be chosen from the class consisting of an anion exchange membrane or cation exchange membrane. In one embodiment, the ion exchange membrane has a polymer structure. The ion exchange membrane polymer structure may be one fluoropolymer or styrene divinyl benzene, or combinations thereof. In another embodiment, the ion exchange membrane may be chosen from the class consisting of Nafion by Dupont; Neosepta CMX, AMX, CIMS, CMB, AHA, ACM, ACS, AFN, AFX by ASTOM Corporation, Selemion by Asahi Glass, or combinations thereof.

The osmagent may be a salt. In one embodiment, the osmagent comprises at least one of ammonium, phosphate, and combinations thereof.

The apparatus includes an extraction chamber and a dispensing chamber that may be separated by one of a flexible diaphragm and a piston, or other displacement members. In one embodiment, the flexible diaphragm comprises or is coated with a low water permeable material. The low water permeable material may be a metal, a metal coated polymer such as metalized PET (polyethylene terephthalate), Halar, PCTFE (polychlorotrifluoroethylene), HDPE (high density polyethylene), PP (polypropylene), PEEK (polyetheretherketone), PET, FEP (fluorinated ethylene propylene) or combinations thereof.

The apparatus in one embodiment may be configured such that at least one of the extraction chamber and the dispensing chamber is at least partially contained within a pouch. The pouch may comprise or be coated with a low or negligible water permeable material. The low or negligible water permeable material may be a metal, a metal coated polymer such as metalized PET (polyethylene terephthalate), Halar, PCTFE (polychlorotrifluoroethylene), HDPE (high density polyethylene), PP (polypropylene), PEEK (polyetheretherketone), PET, FEP (fluorinated ethylene propylene) or combinations thereof.

In one embodiment of the present invention, the beneficial agent comprises a fragrance.

The apparatus may further comprise a circuit to regulate electrical current flowing through the water-transporting membrane, thereby regulating water flowing through the water-transporting membrane into the extraction chamber. The apparatus may further comprise a rate adjustment mechanism to control the rate at which water is received through the water-transporting membrane. The rate adjustment mechanism may be a blind which obscures the water chamber from the water transporting membrane with varying degree.

The apparatus may include a water container that comprises a flexible wall such that the volume changes as water transports across the membrane. The water container may comprise a vent to allow gas to enter the container as water transports across the membrane. In one embodiment, the water container comprises a moveable wall.

A method for delivering a beneficial agent is also disclosed. The method may include the steps of collecting water into water chamber, transporting the water through a water-transporting membrane into an extraction chamber containing an osmagent, thereby expanding the extraction chamber, dispensing a beneficial agent from a dispensing chamber in response to expanding the extraction chamber, and delivering the beneficial agent.

Expanding the extraction chamber may comprise deflecting a flexible diaphragm or moving a piston or other displacement member. The flexible diaphragm may comprise or be coated with a material with low or negligible water permeability. The material with low or negligible water permeability may be a metal, a metal coated polymer such as metalized PET (polyethylene terephthalate), Halar, PCTFE (polychlorotrifluoroethylene), HDPE (high density polyethylene), PP (polypropylene), PEEK (polyetheretherketone), PET, FEP (fluorinated ethylene propylene) or combinations thereof.

The water-transporting membrane may be in communication with the water collection chamber where the membrane has a membrane feature that repels one or more osmagent constituents.

Referring now to FIG. 1a, a close up view of the container 8 is shown having a wicking layer 11 that extends down an outside surface of the container 8 to the port 10 at the base 14 of the device 1. In this case the wicking layer 11 or wick 11 may transport the beneficial agent 2 away from the port 10 and up the side walls of the device 1 so the beneficial agent 2 may more readily evaporate.

Referring now to FIG. 1b, a flexible bellows 4 or diaphragm 4 is shown that enables the volume of the container 3 to reduce as fluid passes through the membrane 5. The bellows 4 preferably comprises or is coated by materials of low water permeability such as metal or barrier polymer such as metalized PET (polyethylene terephthalate), Halar, PCTFE (polychlorotrifluoroethylene).

Figure 2:
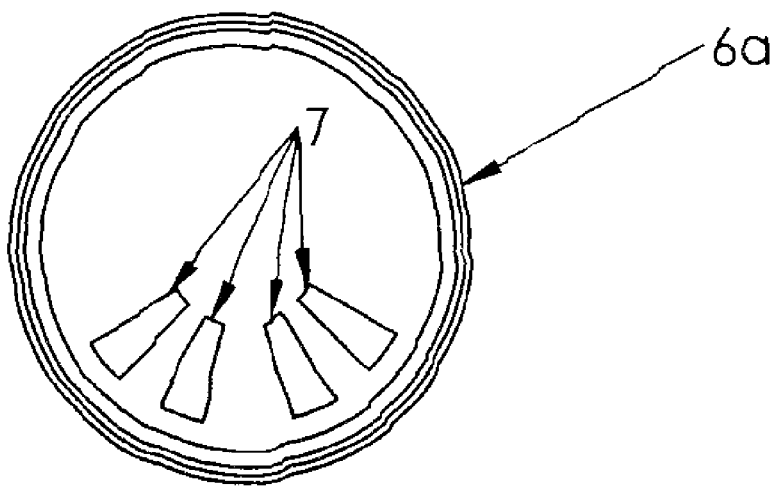
FIG. 2 is a schematic view of a rate adjustment mechanism of FIG. 1.
Figure 3:
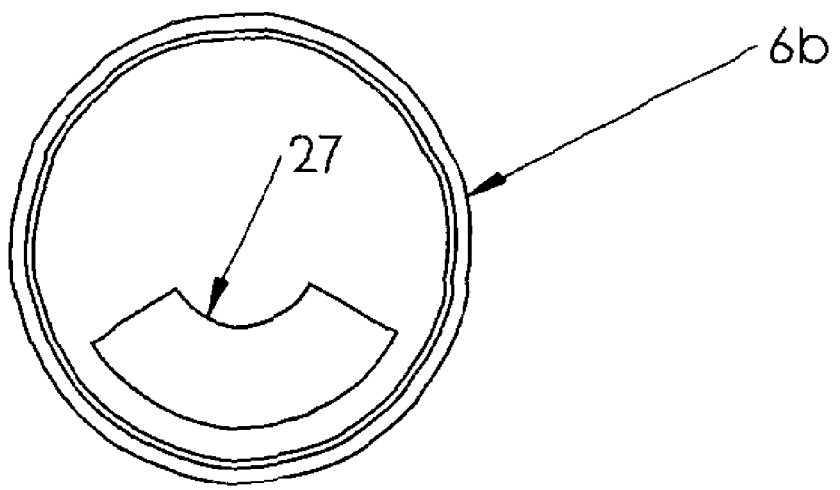
FIG. 3 is a schematic view of a rate adjustment mechanism of FIG. 1.

Referring now to FIGS. 2 and 3, a rate adjustment mechanism is shown. A first adjustment member 6a includes openings 7 radially extending from a midpoint of the first adjustment member 6a. A second adjustment member 6b includes an opening 27. The openings 7 and 27 in respective members 6a and 6b are placed adjacent to each other in the device 1 such that as adjustment member 6a is rotated relative to adjustment member 6b, more or less of the openings 7 and 27 overlap to allow water 9 to access the membrane 5 in different quantities. This in turn affects the rate at which the beneficial agent 2 is dispensed from the device 1. The device 1 also includes one or more vents 12 and 13 to allow gas to enter the container 8 as the water 9 transports across the membrane 5.

Figure 4:
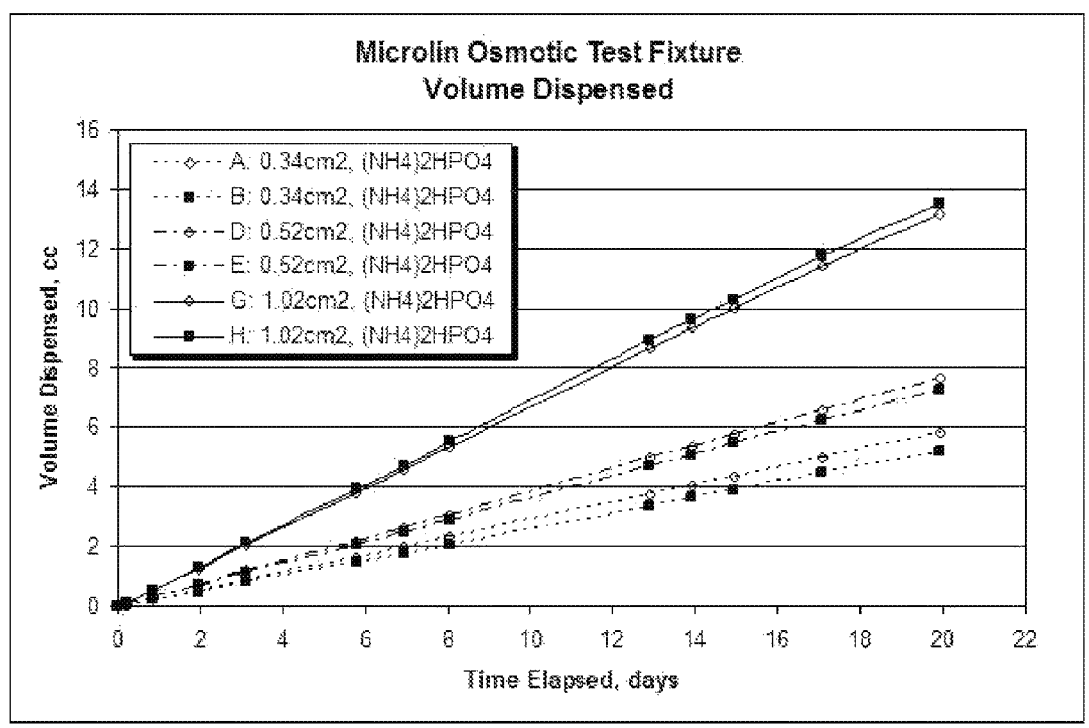
FIG. 4 is table showing the amount of liquid dispensed over a 20-day period for 6 devices utilizing the invention with different membrane areas exposed.
Figure 5:
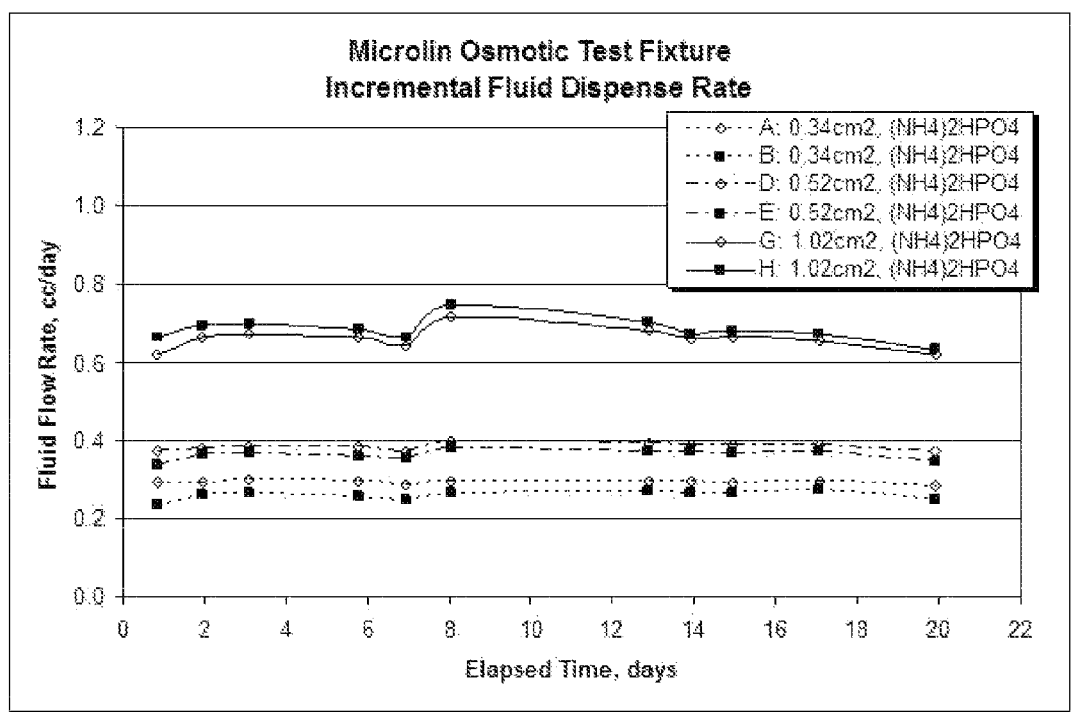
FIG. 5 is a table showing the same data as in FIG. 4 expressed in terms of incremental delivery rate over time.

Referring now to FIGS. 4 and 5, six devices were constructed according to the invention where the ion exchange membrane was Neosepta CMB from Astom Corporation. Two of the devices had 0.342 square centimeters of membrane exposed between an osmagent consisting of saturated ammonium phosphate dibasic and water. Two other of the devices had 0.519 square centimeters of membrane exposed between an osmagent consisting of saturated ammonium phosphate dibasic and water. Two additional devices had 1.026 square centimeters of membrane exposed between an osmagent consisting of saturated ammonium phosphate dibasic and water. Upon activation, the devices delivered beneficial agent approximately in proportion to the area of membrane exposed and at steady rate at shown.

Figure 6:
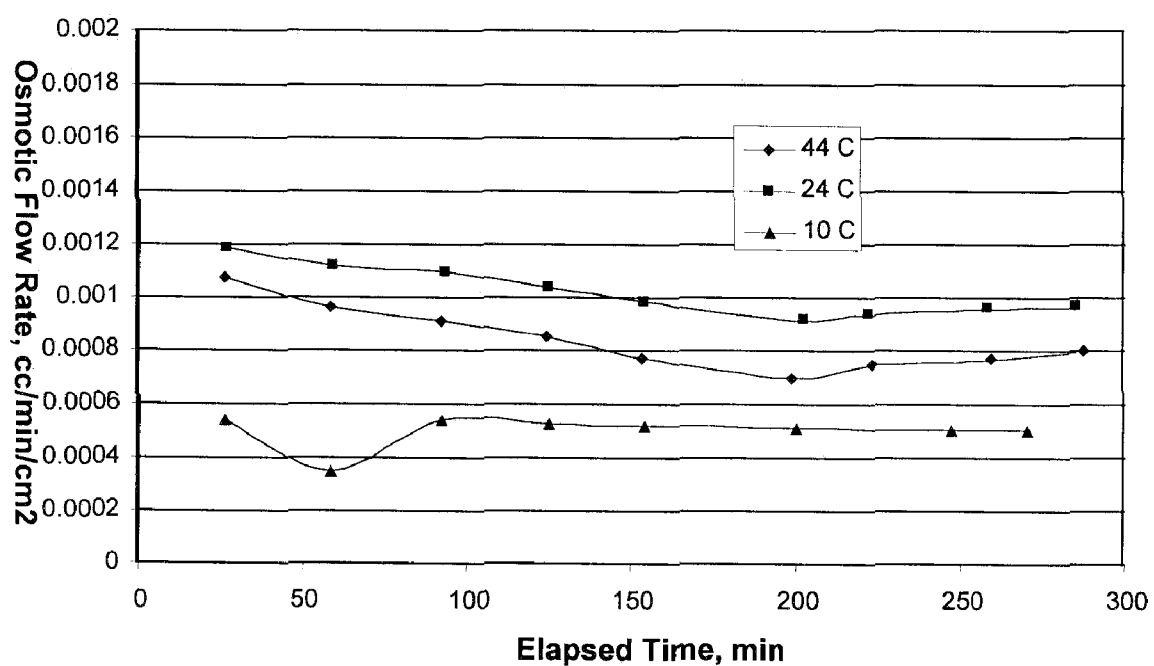
FIG. 6 is a table showing the delivery rate of three devices using the invention each at a different temperature.

Referring to FIG. 6, three devices where constructed according to the teachings of the present invention with a Neosepta CMB membrane and ammonium phosphate dibasic osmagent. The exposed area in each was approximately 10 square centimeters. One device was run at 10° C. temperature, one at 24° C. and one at 44° C. The delivery rate over time is shown. The rate of the 44° C. device was approximately 83% of the rate of the 24° C. device while the rate of the 10° C. device was approximately 52%. These three rates while varied are much closer than they would be if a hydrophobic membrane was used to separate the water from the osmagent and water vapor was required to transport across.

The present invention may be embodied in other specific forms without departing from its basic principles or essential characteristics. The described embodiments are to be considered in all respects as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus to provide controlled delivery of a beneficial agent, the apparatus comprising:
   a water chamber;
   a water-transporting membrane in communication with the water collection chamber, wherein the water-transporting membrane is configured to repel one or more osmagent constituents;
   an extraction chamber to receive water through the water-transporting membrane and into the extraction chamber, thereby expanding the extraction chamber;
   an osmagent in the extraction chamber;
   a dispensing chamber containing a beneficial agent and contracting in response to expanding the extraction chamber; and
   a port in communication with the dispensing chamber to deliver the beneficial agent.

2. The apparatus of claim 1 wherein the water-transporting membrane comprises a functional group on the surface of the water-transporting membrane to repel the one or more osmagent constituents.

3. The apparatus of claim 2 wherein the functional group on the surface of the water-transporting membrane comprises at least one of a quaternary ammonium group and a sulfonate group to repel the one or more osmagent constituents.

4. The apparatus of claim 2 wherein the osmagent comprises at least one of ammonium and phosphate.

5. The apparatus of claim 1 wherein the water-transporting membrane comprises a charged functional group within the water-transporting membrane to repel the one or more osmagent constituents.

6. The apparatus of claim 5 wherein the charged functional group within the water-transporting membrane comprises at least one of a sulfonate and a quaternary ammonium.

7. The apparatus of claim 1 wherein the water-transporting membrane comprises an ion exchange membrane.

8. The apparatus of claim 7 wherein the ion exchange membrane comprises at least one of an anion exchange membrane and a cation exchange membrane.

9. The apparatus of claim 8 wherein the ion exchange membrane comprises at least one of a membrane identified as Nafion by Dupont, a membrane identified as Neosepta CMX, AMX, CIMS, CMB, AHA, ACM, ACS, AFN, or AFX by ASTOM Corporation, and a membrane identified as Selemion by Asahi Glass.

10. The apparatus of claim 7 wherein the ion exchange membrane comprises a polymer structure.

11. The apparatus of claim 10 wherein the ion exchange membrane polymer structure comprises at least one of fluoropolymer and styrene divinyl benzene.

12. The apparatus of claim 1 wherein the osmagent comprises a salt.

* * * * *